United States Patent [19]

Sugasawa et al.

[11] Patent Number: 4,831,132

[45] Date of Patent: May 16, 1989

[54] ORTHO-MONO-SUBSTITUTED AMINO)PHENYLIMINES

[75] Inventors: Tsutomu Sugasawa, Hyogo; Kazuyuki Sasakura, Nara, both of Japan

[73] Assignee: Shionogi & Co., Ltd., Osaka, Japan

[21] Appl. No.: 948,119

[22] Filed: Dec. 30, 1986

Related U.S. Application Data

[60] Division of Ser. No. 837,647, Mar. 5, 1986, abandoned, which is a continuation of Ser. No. 627,732, Jul. 3, 1984, abandoned.

[30] Foreign Application Priority Data

Jul. 13, 1983 [JP] Japan ................... 58-128158

[51] Int. Cl.$^4$ ............... C07D 225/06; C07C 85/18
[52] U.S. Cl. ................... 540/476; 540/593; 546/166; 546/223; 548/557; 548/559; 564/269; 564/272; 564/274; 564/275
[58] Field of Search ............ 564/329, 269, 272; 546/223, 166; 548/557, 558, 559, , 490; 540/476, 593

[56] References Cited

U.S. PATENT DOCUMENTS

| | | | |
|---|---|---|---|
| 3,431,304 | 3/1969 | Fryer et al. | 564/269 |
| 3,440,281 | 4/1969 | Fryer et al. | 564/269 |
| 4,045,576 | 8/1977 | Welstead, Jr. et al. | 562/441 |
| 4,160,784 | 7/1979 | Sugasawa et al. | 564/269 |
| 4,560,684 | 12/1985 | Sugasawa et al. | 548/557 |

OTHER PUBLICATIONS

Sugasawa et al. II, "Aminohaloforane in Organic, etc" JACS 100 (1978) 4842.

Huggett et al., "The Relative Lewis Acidities, etc" CA 93: 138590u.

Sasakura et al, "Aminohaloborane in Organic, etc.", Chem. Pharm. Bull. 33 1836 (1985).

Sugasawa, "Ortho-exclusive Friedel-Crafts etc." Yoshida, ed. New Synthetic Methodology, etc. (1986).

*Primary Examiner*—Richard L. Raymond
*Assistant Examiner*—Patricia C. Morris
*Attorney, Agent, or Firm*—Wenderoth, Lind & Ponack

[57] ABSTRACT

Novel ortho-(mono-substituted amino)phenylimines being intermediates to psychotropic drugs and other drugs are economically and industrially prepared by reacting anilines with nitriles in the presence of a boron trifluoride ether adduct and a halide-type Lewis acid, if necessary together with an organic base. Furthermore, the imines can be hydrolyzed with an acid to afford the corresponding ketones.

1 Claim, No Drawings

ORTHO-(MONO-SUBSTITUTED AMINO)PHENYLIMINES

This is a division of Ser. No. 837,647, filed Mar. 5, 1986, now abandoned, which is a continuation of Ser. No. 627,732, filed July 3, 1984, now abandoned.

BACKGROUND OF THE INVENTION

1. Field of the Invention

The present invention relates to intermediates for psychotropic 1,4-benzodiazepines and/or anti-inflammatory amfenac (2-amino-3-benzoyl phenylacetic acid).

2. Prior Art

The present inventors have developed a process for preparing a 2-aminobenzophenone derivative which comprises acylating selectively an aniline at the ortho position with a benzonitrile in the presence of boron trichloride and a Lewis acid (e.g., aluminum chloride) [U.S. Pat. No. 4,160,784; J. Am. Chem. Soc., 100, 4842 (1978)] as described in the following reaction sequence.

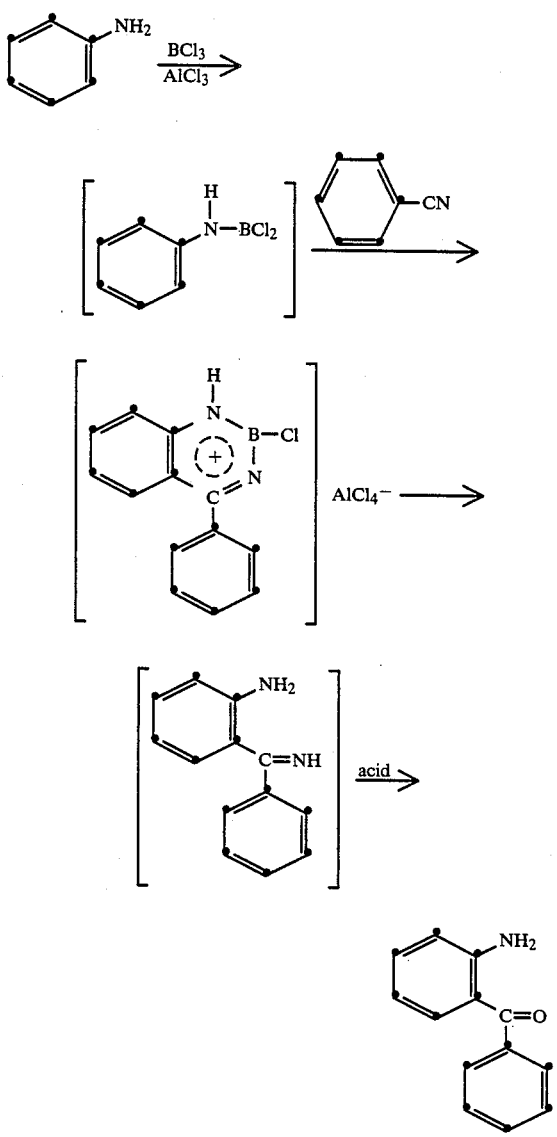

Note The structural formulae in the brackets havenot yet been identified.

BRIEF SUMMARY OF THE INVENTION

The present invention relates to an ortho-(monosubstituted amino)phenylimine derivative or its acid addition salt, its production, and use of the product. More particularly, this invention relates to an imine (I):

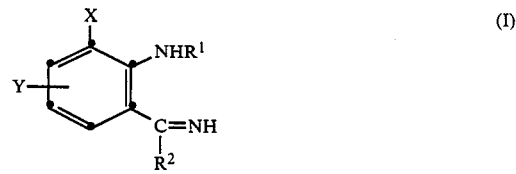

(wherein $R^1$ is $C_3$–$C_5$ branched chain alkyl, $C_3$–$C_{15}$ dialkylaminoalkyl, piperidinyl, 1-($C_1$–$C_5$ alkyl)piperidinyl, pyrrolidinyl, or 1-(phenyl $C_1$–$C_5$ alkyl)pyrrolidinyl; $R^2$ is $C_1$–$C_5$ alkyl, phenyl, or halogenophenyl; X is hydrogen, halogen, $C_1$–$C_5$ alkyl, $C_1$–$C_5$ alkoxy, or taken together with $R^1$ may form $C_2$–$C_5$ alkylene; Y is hydrogen, halogen, $C_1$–$C_5$ alkyl, or $C_1$–$C_5$ alkoxy) or its acid addition salt.

The imine (I) can be prepared by reacting an aniline of the formula (II):

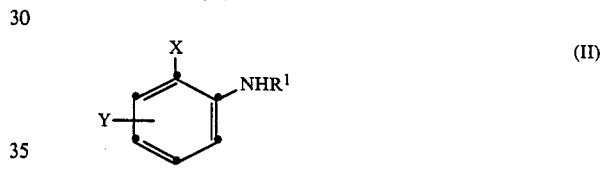

(wherein $R^1$, X, and Y each has the same significance as defined above) with a nitrile of the formula (III):

$$R^2-CN \quad (III)$$

(wherein $R^2$ has the same significance as defined above) in the presence of a boron trifluoride ether adduct and a halide-type Lewis acid, if necessary together with an organic base.

Further, the imine (I) can be hydrolyzed with an acid to produce a ketone of the formula (IV).

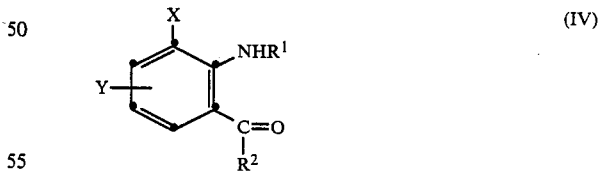

(wherein $R^1$, $R^2$, X, and Y each has the same significance as defined above).

The inventors of the present invention have investigated a process for preparing the imines (I) or the ketones (IV) being intermediates for some psychotropic drugs and other drugs. They have found that industrially less expensive boron trifluoride ether adducts can be used instead of boron trichloride in the presence of a halide-type Lewis acid in producing novel intermediates, the imines (I) in which the nitrogen atom is substituted by $R^1$ as defined above, the present invention is based on this finding.

DETAILED DESCRIPTION OF THE INVENTION

The terms used in the definition of the formulae (I) to (IV) are illustratively explained below: the $C_1$-$C_5$ alkyl includes methyl, ethyl, n-propyl, isopropyl, n-butyl, isobutyl, sec-butyl, tert-butyl, n-pentyl, isopentyl, neopentyl, tert-pentyl, and the like; the $C_3$-$C_5$ branched chain alkyl includes isopropyl, isobutyl, sec-butyl, tert-butyl, isopentyl, neopentyl, tert-pentyl, and the like; the $C_3$-$C_{15}$ dialkylaminoalkyl means the $C_1$-$C_5$ alkyl which is substituted by $C_2$-$C_{10}$ dialkylamino, for example dimethylaminoethyl, diethylaminoethyl, dipropylaminoethyl, dibutylaminopropyl, dimethylaminopentyl, and the like; the $C_2$-$C_5$ alkylene includes ethylene, trimethylene, 1,2-propylene, and the like; concerning the 1-($C_1$-$C_5$ alkyl)piperidinyl, the $C_1$-$C_5$ alkyl means the same significance as mentioned above and the piperidinyl means 2-, 3-, or 4-piperidinyl, and exemplary 1-($C_1$-$C_5$ alkyl)piperidinyl is 1-methyl-4-piperidinyl, 1-ethyl-3-piperidinyl, and 1-(n-propyl)-2-piperidinyl; in the 1-(phenyl $C_1$-$C_5$ alkyl)pyrrolidinyl, the phenyl $C_1$-$C_5$ alkyl includes benzyl, phenethyl, phenylpropyl, phenylbutyl, phenylpentyl, and the like, the pyrrolidinyl means 2- or 3- pyrrolidinyl; the $C_1$-$C_5$ alkoxy includes methoxy, ethoxy, n-propoxy, isopropoxy, n-butoxy, isobutoxy, n-pentyloxy, and the like; the halogen includes fluorine, chlorine, bromine, and iodine; and the halogenophenyl includes fluorophenyl, chlorophenyl, bromophenyl, and the like.

According to the present invention, the imines (I) can be prepared by reacting the anilines (II) with the nitriles (III) in the presence of a boron trifluoride ether adduct and a halide-type Lewis acid, if necessary together with an organic base, and the imines (I) can be converted into the ketones (IV) by hydrolyzing with an acid as shown in the following reaction sequence.

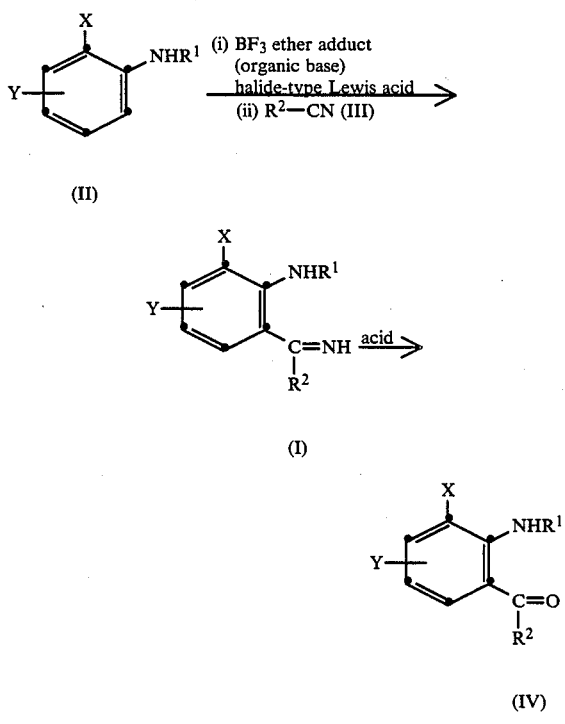

The reaction of the anilines (II) with the nitriles (III) is carried out in the presence or absence of an appropriate solvent at a temperature of about 20° to about 200° C., preferably about 50° to about 180° C., and terminates within a period of several hours. The resulting mixture is treated with an inorganic base or a weak acid in a conventional manner to give the imines (I). As the solvent, halogenohydrocarbons including dichloromethane, 1,2-dichloroethane, chloroform, carbon tetrachloride, and the like and aromatic solvents including benzene, toluene, xylene, and the like may be exemplified. The boron trifluoride ether adduct includes diethyl ether adduct, di-n-butyl ether adduct, and the like. The halide-type Lewis acid illustratively includes silicon tetrachloride, aluminum chloride, aluminum bromide, titanium tetrachloride, phosphorus trichloride, phosphorus pentachloride, phosphorus oxychloride, and the like, and especially the silicon tetrachloride is preferred. The organic base which, if necessary, is used illustratively includes tertiary amines (e.g., triethylamine, dimethylethylamine, dimethylpropylamine, tri-n-butylamine, diisopropylethylamine, N-methylpiperidine, N-ethylpiperidine, N-methylpyrrolidine, N-ethylpyrrolidine, etc.), 2,6-lutidine, and the like.

As the inorganic base alkali metal hydroxide (e.g., lithium hydroxide, sodium hydroxide, and potassium hydroxide), alkali metal carbonate (e.g., sodium carbonate and potassium carbonate), and the like may be employed. The weak acid includes acetic acid, and the like.

The imines (I) can be converted into the ketones (IV) as mentioned above by hydrolyzing with an acid at a temperature of about 30° to about 150° C., preferably about 60° to about 120° C. As the acid, strong acids such as hydrochloric acid, sulfuric acid, and the like may be employed. After the reaction of the anilines (II) with the nitriles (III), the reaction mixture can be hydrolyzed directly with an acid to give the ketones (IV). The whole reactions can be conducted in a single reaction vessel by a simple operation.

The imines (I) prepared in the process described above can be converted into corresponding salts by treating with an organic or inorganic acid (e.g., maleic acid, oxalic acid, acetic acid, methanesulfonic acid, phosphoric acid, etc.).

The imines (I) and the ketones (IV) are useful as the intermediates to 1,4-benzodiazepines which are valuable as psychotropic drugs such as antianxiety agents, antidepressants, and hypnotics [For example, U.K. Unexamined Patent Publn. No. 2,133,008]. Furthermore, other drugs can be derived from the ketones (IV), for example, 7-benzoyl-indoline, one of the ketones (IV) is useful as an intermediate to anit-inflammatory drug, amfenac, (2-amino-3-benzoyl-phenylacetic acid) [U.S. Pat. No. 4,045,576].

The imines (I) prepared in the process described above are exemplified below.

2-(1-Methyl-4-piperidinyl)aminobenzophenone imine;
2-(1-Methyl-4-piperidinyl)amino-5-chloro-2'-fluorobenzophenone imine;
2-(1-Methyl-4-piperidinyl)aminoacetophenone imine;
2-(1-Methyl-4-piperidinyl)amino-5-methyl-2'-chlorobenzophenone imine;
2-(1-Methyl-4-piperidinyl)amino-5-methoxy-2'-fluorobenzophenone imine;
2-(1,1'-Diethylaminoethyl)aminobenzophenone imine;
2-(1-Methyl-4-piperidinyl)amino-5-chlorobenzophenone imine;
2-(1-Methyl-4-piperidinyl)amino-5-chloro-2'-chlorobenzophenone imine;

2-(1-Methyl-4-piperidinyl)amino-5-fluorobenzophenone imine;
2-(1-Methyl-4-piperidinyl)amino-5-fluoro-2'-fluorobenzophenone imine;
2-(1-Methyl-4-piperidinyl)amino-5-fluoro-2'-chlorobenzophenone imine;
2-(1-Methyl-4-piperidinyl)amino-5-bromobenzophenone imine;
2-(1-Benzyl-3-pyrrolidinyl)amino-5-chloro-2'-fluorobenzophenone imine;
7-(2-iminobenzyl) indoline.

The present invention will be explained in more detail by the following Examples and Reference Example.

EXAMPLE 1

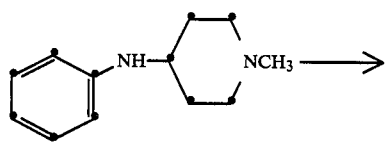

1

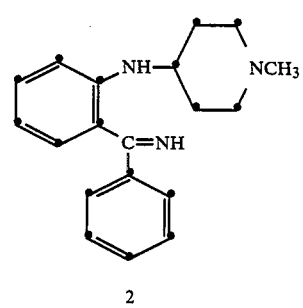

2

To a solution of 0.38 g (2 mmol) of 4-anilino-1-methyl-piperidine 1 dissolved in 10 ml of 1.2-dichloroethane are added 0.3 ml (2×1.2 mmol) of boron trifluoride ether adduct, 0.28 ml (2×1.2 mmol) of silicon tetrachloride, and 0.41 ml (2×2 mmol) of benzonitrile at room temperature with stirring, and the mixture is heated under reflux with stirring for 20 hours. The reaction mixture is cooled and a solution of 2.5 g of sodium hydroxide dissolved in 10 ml of water and 4 ml of methanol are added thereto with stirring under ice-cooling. The mixture is stirred at room temperature for 1 hour and extracted with dichloromethane; the organic layer is washed with water, dried over anhydrous magnesium sulfate, and concentrated. The resulting residue is recrystallized from ether-petroleum ether to give 414 mg of crystalline 2-(1-methyl-4-piperidinyl)aminobenzophenone imine 2.

m.p.: 116°–117° C.
Yield: 71%.
Anal. Calcd. (%) (for $C_{19}H_{23}N_3$): C, 77.77; H, 7.80; N, 14.32. Found (%): C, 78.00; H, 7.91; N, 14.26.
IR: $\nu_{max}^{CHCl_3}$ 3280, 1608 cm$^{-1}$.
$^1$HNMR, $\delta^{CDCl_3}$: 1.5–3.0 (8H, m, aliph. H), 2.38 (3H, s, NCH$_3$), 3.55 (1H, m,

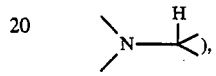

6.3–7.4 (9H, m, arom, H), 9.38 (1H, s, =NH), 9.67 (1H, d, J=7 Hz,

—NH—◁).

EXAMPLES 2-13

In the same manner as in Example 1, the following starting materials (IIa) is allowed to react with the starting materials (III) to give the corresponding objective compounds (Ia) described in Table 1.

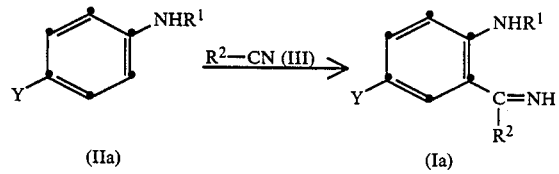

TABLE 1

| Ex. Nos. | Y | R¹ | R² | m.p. (°C.) | Yield (%) |
|---|---|---|---|---|---|
| 2 | Cl | ⌬NCH₃ | F-phenyl | 145–146 | 80 |
| 3 | H | " | —CH₃ | 92–99 | 66 |
| 4 | CH₃ | " | Cl-phenyl | 111–113 | 72 |
| 5 | CH₃O | " | F-phenyl | 132–134 | 40 |

TABLE 1-continued

| Ex. Nos. | Y | R¹ | R² | m.p. (°C.) | Yield (%) |
|---|---|---|---|---|---|
| 6 | H |  -(CH₂)₂-N(C₂H₅)(C₂H₅) |  phenyl | oil*¹ | 78 |
| 7 | Cl |  NCH₃ piperidine | phenyl | 115–117 | 92 |
| 8 | Cl | " | Cl-phenyl | 157–159 | 90 |
| 9 | F | " | phenyl | 130–131 | 85 |
| 10 | F | " | F-phenyl | 131–132 | 90 |
| 11 | F | " | Cl-phenyl | 138–139 | 90 |
| 12 | Br | " | phenyl | 110–112 | 85 |
| 13 | Cl |  NCH₂Ph *2 | F-phenyl | oil*³ | 90 |

*¹ ¹HNMR, δ^CDCL₃: 1.07(t, J=6 Hz, CH₂CH₃), 2.4–2.8 (m, aliph. H), 3.32 (q, J=6 Hz, —HNCH₂CH₂N), 6.4–7.7 (m, arom. H), 8.65(broad s, —NH—CH₂), 9.45 (s, =NH).
*²The abbreviation, Ph means phenyl.
*³IR, ν$_{max}^{CHCl_3}$ 3280, 3190 cm⁻¹. ¹HNMR, δ^CDCl₃: 3.63 (2H, s, NCH₂—Ph), 9.50 (1H, s, =NH), 9.83 (1H, d, J=7 Hz, NH).
Note: In Examples 7–13, 2 × 2.0 mmol of boron trifluoride ether adduct and 2 × 2.0 mmol of silicon tetrachloride are employed.

EXAMPLE 14

3

→

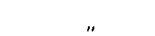

4

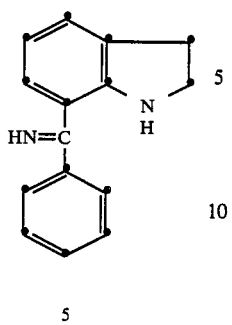

To a solution of 357 mg (3 mmol) of indoline 3 dissolved in 10 ml of 1,2-dichloroethane are added 0.5 ml (3×1.2 mmol) of triethylamine, 0.44 ml (3×1.2 mmol) of boron trifluoride ether adduct, 0.43 ml (3×1.2 mmol) of silicon tetrachloride, and 0.62 ml (3×2 mmol) of benzonitrile at room temperature with stirring, and the mixture is heated under reflux for 4 hours. The mixture is cooled and a solution of 4 g of sodium hydroxide dissolved in 15 ml of water is added thereto under ice-cooling. The mixture is stirred at room temperature for 2 hours, and the reaction mixture is extracted with a mixture of dichloromethane:ethanol (3:1). The organic layer is washed with water and concentrated, and the resulting residue is recrystallized from a mixture of dichloromethane and ethanol to give 400 mg of 7-[α-(diethoxyborylimino)benzyl]indoline 4 as crystals (m.p.: 160°–163° C.).

To a solution of 400 mg (1.24×1.3 mmol) of the compound provided in the above step and 16 ml of benzene is added 16.2 ml (1.24×1.3 mmol) of 0.1N acetic acid, and the mixture is stirred at room temperature for 5 minutes. The reaction mixture is mixed with 2N sodium hydroxide and extracted with ether. The ether layer is washed with water, dried over anhydrous potassium carbonate, and concentrated. The residue is recrystallized from ether-petroleum ether to give 222 mg of 7-(2-iminobenzyl)indoline 5 as crystals.

m.p.: 62°–63° C.
Yield: 33%.

Anal. Calcd. (%) (for $C_{15}H_{14}N_2$): C, 81.05; H, 6.35; N, 12.60. Found (%): C, 81.40; H, 6.22; N, 12.20.

$^1$HNMR, $\delta^{CDCl_3}$: 2.9–3.9 (4H, m, aliph. H), 6.3–7.5 (9H, m, arom. H and NH), 9.35 (1H, s, =NH).

EXAMPLE 15

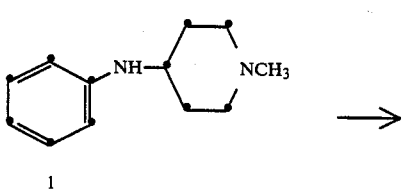

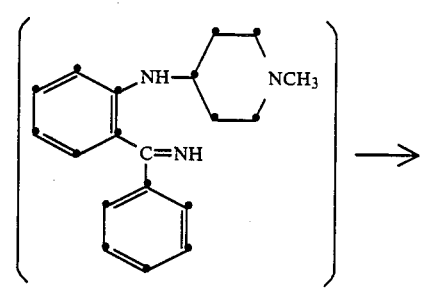

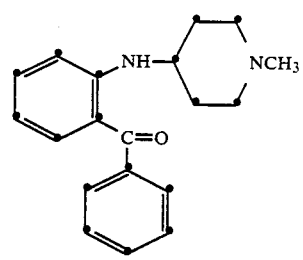

To a solution of 0.38 g (2 mmol) of 4-anilino-1-methylpiperidine 1 dissolved in 10 ml of 1,2-dichloroethane are added 0.3 ml (2×1.2 mmol) of boron trifluoride ether adduct, 0.28 ml (2×1.2 mmol) of silicon tetrachloride, and 0.41 ml (2×2 mmol) of benzonitrile, and the mixture is heated under reflux for 20 hours and then cooled. The reaction mixture is mixed with 5 ml of 6N hydrochloric acid and refluxed for 20 hours. The mixture is cooled and washed with ether, and the resulting aqueous layer is basified with potassium carbonate and extracted with dichloromethane. The dichloromethane layer is washed with water, dried over anhydrous potassium carbonate, and concentrated under reduced pressure. The residue is chromatographed on a column of 2.8 g of silica-gel and eluted with dichloromethane containing 2% methanol to give 466 mg of 2-(1-methyl-4-piperidinyl)aminobenzophenone 6 as oily material.

Yield: 79%

As the dihydrobromide, m.p.: 193°–203° C.

0.2 mmol of the 4-anilino-1-methylpiperidine 1 (10% of the starting material) is recovered.

EXAMPLES 16–17

In the same manner as in Example 15, the compounds (IVb) described in Table 2 are prepared by reacting the following starting materials (IIb) with the starting materials (III) through the compounds (Ib).

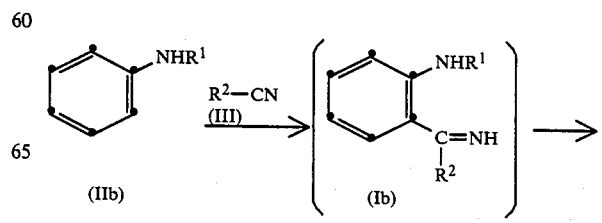

minutes and then treated in the same manner as in Example 15 to give 599 mg of 2-(1-methyl-4-piperidinyl)aminobenzophenone 6 as oily material.

Yield: 95%

When the reaction is carried out in the absence of a halide-type Lewis acid, the yield of the compound 6 is about 25%.

EXAMPLES 19-29

In the same manner as in Example 18, the mixture of the starting materials (IIc), boron trifluoride ether adduct, and a halide-type Lewis acid dissolved in a solvent is heated, and the reaction mixture is evaporated and then the compounds (III) are added thereto to yield the corresponding objective compounds (IVc) described in Table 3 through the compounds (Ic).

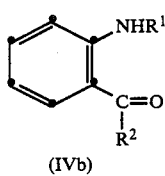

(IVb)

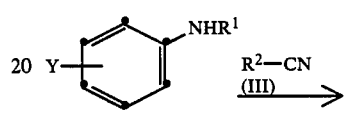

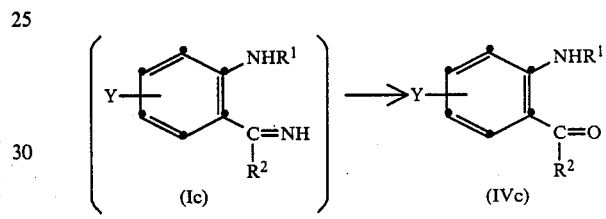

TABLE 2

| Ex. Nos. | $R^1$ | $R^2$ | IR (cm$^{-1}$) | Yield (%) |
|---|---|---|---|---|
| 16 | —piperidinyl-NCH$_3$ | CH$_3$ | 3260, 1630 (film) | 85 |
| 17 | —(CH$_2$)$_2$—N(C$_2$H$_5$)$_2$ | CH$_3$ | 3280, 1640 (film) | 54 |

EXAMPLE 18

To a solution of 0.38 g (2 mmol) of 4-anilino-1-methylpiperidine 1 dissolved in 10 ml of 1,2-dichloroethane are added 0.3 ml (2×1.2 mmol) of boron trifluoride ether adduct and 0.28 ml (2×1.2 mmol) of silicon tetrachloride, and the mixture is heated under reflux for 2 hours. The reaction mixture is evaporated, and 0.4 ml (2×2 mmol) of benzonitrile is added to the resulting residue. The mixture is heated at 160° C. for 1.5 hours and cooled, and then mixed with 5 ml of 6N hydrochloric acid. The reaction mixture is stirred at 100° C. for 20

TABLE 3

| Ex. Nos. | Y | $R^1$ | $R^2$ | Halide-type Lewis acid | m.p. (°C.) (IR cm$^{-1}$) | Yield (%) |
|---|---|---|---|---|---|---|
| 19 | H | —piperidinyl-NCH$_3$ | —C$_6$H$_5$ | AlBr$_3$ | 193-203 (2HBr) | 60 |
| 20 | " | " | " | AlCl$_3$ | 193-203 (2HBr) | 69 |
| 21 | " | " | " | TiCl$_4$ | 193-203 (2HBr) | 34 |
| 22 | " | " | " | PCl$_3$ | 193-203 (2HBr) | 38 |
| 23 | " | " | " | PCl$_5$ | 193-203 (2HBr) | 49 |
| 24 | " | —(CH$_2$)$_2$N(C$_2$H$_5$)$_2$ | " | SiCl$_4$ | 51-53 | 73 |
| 25 | 3-CH$_3$ | —CH(CH$_3$)$_2$ | —C$_6$H$_4$F | SiCl$_4$ | 123-124 | 14 |
| 26 | 4-Cl | —piperidinyl-NCH$_3$ | —C$_6$H$_4$F | " | (3280, 1610 (film)) | 82 |
| 27 | 4-CH$_3$ | " | " | " | (3280, 1620 (film)) | 90 |
| 28 | 4-CH$_3$O | " | " | " | 117-118 | 53 |
| 29 | 3-F | " | " | " | 118-120 | 35 |

EXAMPLE 30

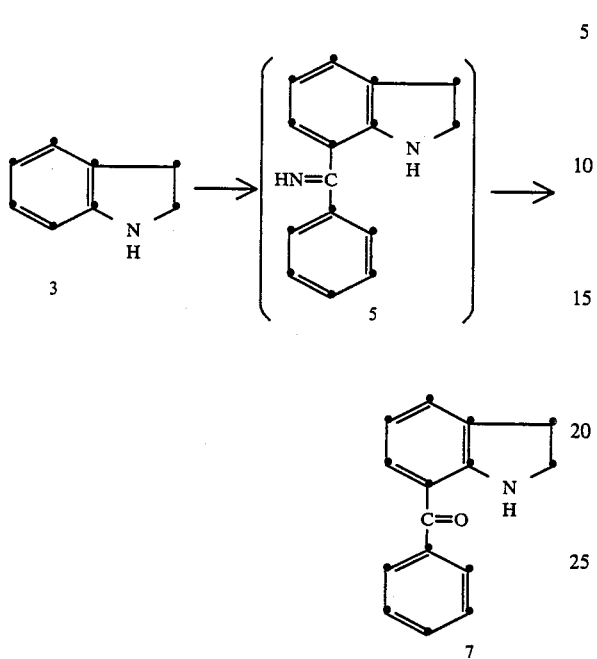

To a solution of 357 mg (3 mmol) of indoline 3 dissolved in 10 ml of 1,2-dichloroethane are added 0.5 ml (3×1.2 mmol) of triethylamine, 0.44 ml (3×1.2 mmol) of boron trifluoride ether adduct, and 0.43 ml (3×1.2 mmol) of silicon tetrachloride, and the mixture is heated under reflux with stirring for 2 hours. The reaction mixture is evaporated; 0.62 ml (3×2 mmol) of benzonitrile is added to the residue and the mixture is heated at 160° C. with stirring for 5 hours and then cooled. The mixture is mixed with 5 ml of 6N hydrochloric acid and heated at 100° C. for 20 minutes. The reaction mixture is basified with potassium carbonate and extracted with dichloromethane. The organic layer is washed with water, dried over anhydrous potassium carbonate, and concentrated. The residue is chromatographed on a column of 4.6 g of silica-gel and eluted with dichloromethane. The eluate from dichloromethane is concentrated. The residue is recrystallized from ether-petroleum either to give 555 mg of 7-benzoylindoline 7 as crystals.

m.p.: 124°–125° C.

Yield: 83%

REFERENCE EXAMPLE

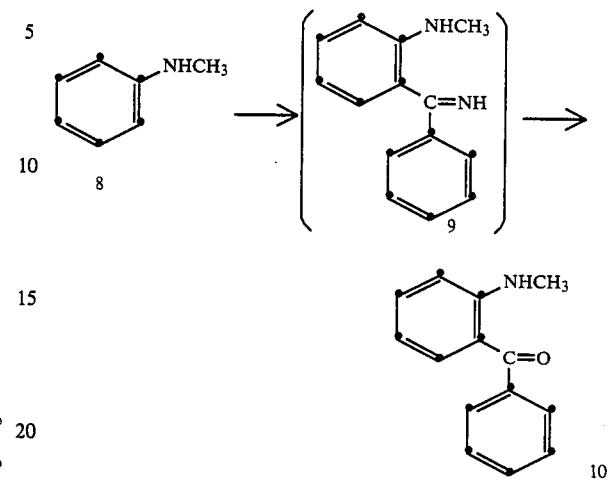

In the same manner as in Example 30, 2-(N-methylamino)benzophenone 10 is prepared from N-methylaniline in the presence of triethylamine as an organic base. Yield: 62%

When diisopropylethylamine is employed as the organic base in the reaction mentioned above, yield of the objective compound 10 is 63%; and when 2,6-lutidine is employed, yield of the objective compound 10 is 59%.

What we claim is:

1. A process for preparing a compound of the formula:

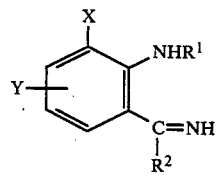

wherein $R^1$ is $C_3-C_5$ branched chain alkyl, $C_3-C_{15}$ dialkylaminoalkyl, piperidinyl, 1-($C_1-C_5$ alkyl)piperidinyl, pyrrolidinyl, or 1-(phenyl $C_1-C_5$ alkyl)pyrrolidinyl; $R^2$ is $C_1-C_5$ alkyl, phenyl, or halogenophenyl; X is hydrogen, halogen, $C_1-C_5$ alkyl, $C_1-C_5$ alkoxy or taken together with $R^1$ may form $C_2-C_5$ alkylene; and Y is hydrogen, halogen, $C_1-C_5$ alkyl, or $C_1-C_5$ alkoxy; which comprises reacting an aniline of the formula:

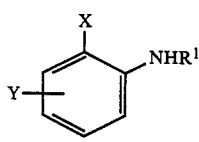

wherein $R^1$, X, and Y each has the same significance as defined above; with a nitrile of the formula:

wherein $R^2$ has the same significance as defined above; in the presence of a boron trifluoride either adduct and silicon tetrachloride in a solvent.

* * * * *